United States Patent
Grahn et al.

(10) Patent No.: US 7,182,776 B2
(45) Date of Patent: *Feb. 27, 2007

(54) METHODS AND DEVICES FOR MANIPULATING THE THERMOREGULATORY STATUS OF A MAMMAL

(75) Inventors: Dennis A. Grahn, Palo Alto, CA (US); H. Craig Heller, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/932,344

(22) Filed: Aug. 31, 2004

(65) Prior Publication Data

US 2005/0085882 A1 Apr. 21, 2005

Related U.S. Application Data

(63) Continuation of application No. PCT/US02/09772, filed on Mar. 29, 2002, which is a continuation-in-part of application No. 09/878,129, filed on Jun. 7, 2001, now Pat. No. 6,602,277.

(60) Provisional application No. 60/210,659, filed on Jun. 9, 2000.

(51) Int. Cl.
A61F 7/00 (2006.01)

(52) U.S. Cl. ...................... 607/104; 607/107

(58) Field of Classification Search .................. 607/96, 607/104, 108, 109
See application file for complete search history.

(56) References Cited

U.S. PATENT DOCUMENTS 4,987,896 A * 1/1991 Nakamatsu .................. 607/109

(Continued)

FOREIGN PATENT DOCUMENTS

WO WO98/40039 9/1998

OTHER PUBLICATIONS

Soreide et al. "A Non-Invasive Means to Effectively Restore Normothermia in Cold Stressed Individuals: A Preliminary Report," (1999) *The Journal of Emergency Medicine*, 17(4):725-730.

(Continued)

*Primary Examiner*—Roy D. Gibson
(74) *Attorney, Agent, or Firm*—Bret E. Field; James S. Nolan; Bozicevic, Field & Francis LLP

(57) ABSTRACT

Methods and devices for manipulating the thermoregulatory status of a mammal are provided. In the subject methods, thermal energy is transferred between the environment and both of the thoracic/abdominal core body and head of the mammal. In general, thermal energy transfer between thoracic/abdominal core body and the environment occurs under negative pressure conditions. The subject methods and devices can be used to increase the thoracic/abdominal core body temperature of a mammal, in which case thermal energy is introduced into the thoracic/abdominal core body of the mammal and removed from the head of the mammal or cold is merely applied thereto. The subject methods and devices can also be used to reduce the thoracic/abdominal core body temperature of a mammal, in which case thermal energy is removed from the thoracic/abdominal core body of the mammal and introduced into the head of the mammal or heat is merely applied thereto.

27 Claims, 5 Drawing Sheets

U.S. PATENT DOCUMENTS 5,683,438 A     11/1997   Grahn
6,149,674 A     11/2000   Borders et al.
6,228,106 B1 *   5/2001   Simbruner et al. ........... 607/96

OTHER PUBLICATIONS

Grahn et al. "Recovery from Mild Hypothermia can be Accelerated by Mechanically Distending Blood Vessels in the Hand," (1998) *The American Physiological Society*, http://www.jap.org 1643-1648.

Wachter, "New Device Could Reduce Rewarming Time from Anesthesia Hypothermia," Anesthesiology News (1997), p. 1.

"Hypothermia Rewarmer Launched in Postoperative Market (Dec. 4, 1998)," MDI Business Advisor (1998).

Thermo-STAT Operations Manual, Aquarius Medical Corporation, (1998).

\* cited by examiner

FIG. 5
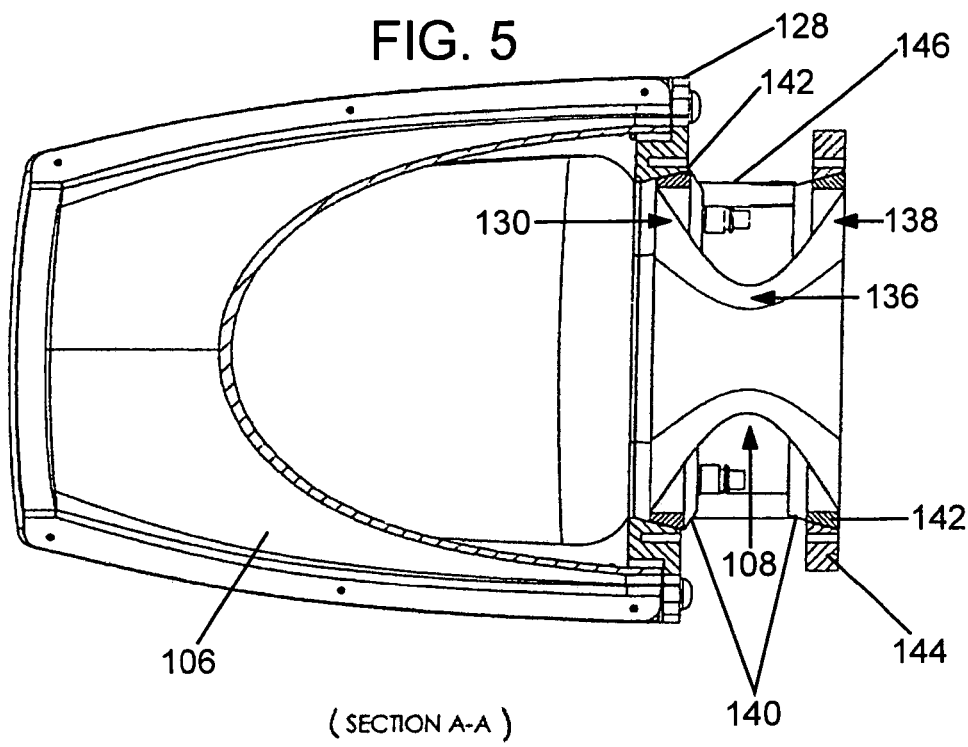
(SECTION A-A)
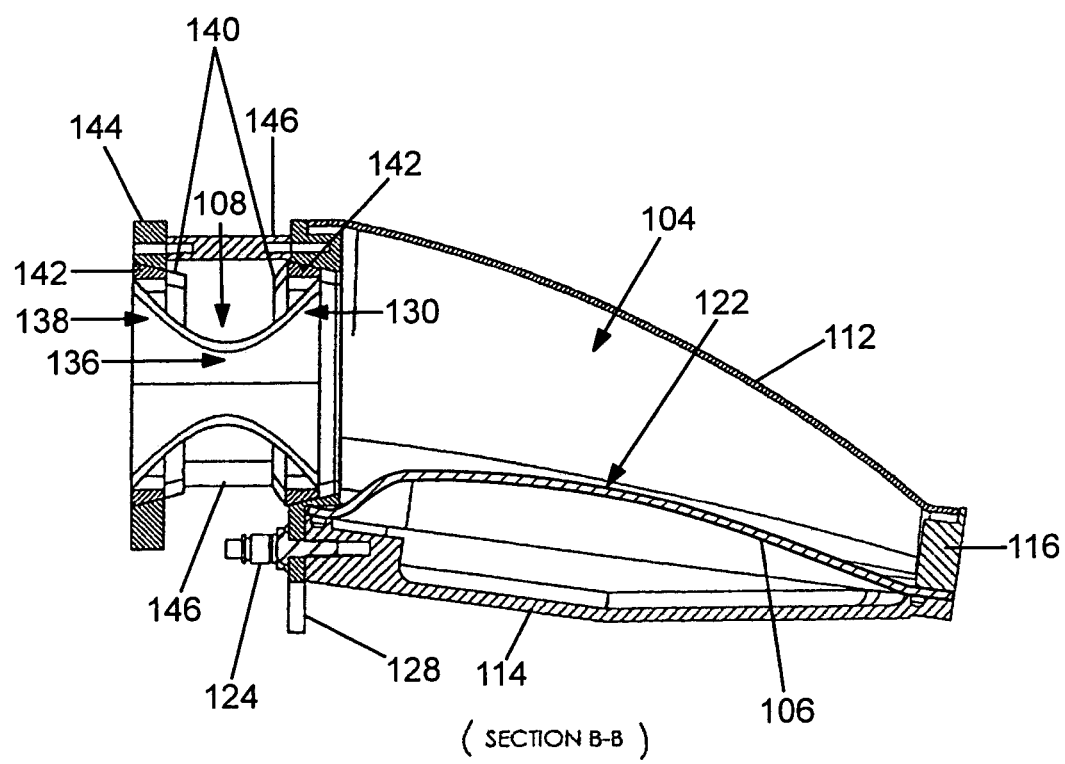
(SECTION B-B)
FIG. 6

METHODS AND DEVICES FOR MANIPULATING THE THERMOREGULATORY STATUS OF A MAMMAL

CROSS-REFERENCE TO RELATED APPLICATIONS

This application is to be a continuing application of U.S. patent application Ser. No. 09/878,129, pending, which, pursuant to 35 U.S.C. § 119(e) claims benefit to the filing date of the U.S. Provisional Patent Application Ser. No. 60/210,659 filed Jun. 9, 2000; the disclosures of each are herein incorporated by reference in their entirety.

INTRODUCTION

1. Field of the Invention

The field of this invention is the thermoregulatory status of mammals.

2. Background of the Invention

Human body temperature is normally tightly controlled by an autonomic regulatory system referred to herein as the thermoregulatory system. The most important or, at least, a primary effector of this regulatory system is blood flow to specialized skin areas where heat from the deep body core can be dissipated to the environment. Normally, when body and/or environmental temperatures are high, the dilation of certain blood vessels favors high blood flow to these surfaces, and as environmental and/or body temperatures fall, vasoconstriction reduces blood flow to these surfaces and minimizes heat loss to the environment.

There are situations, however, in which it would be desirable to be able to manipulate the transfer of heat across the skin surfaces to provide for regions of different temperature in the mammalian body, i.e., to provide for a temperature gradient in the body made up of at least two different temperature compartments. Such temperature compartmentalization would be useful in a number of applications, including therapeutic treatment regimens, as described in greater detail below. However, temperature compartmentalization of the mammalian body is difficult to produce, as attempts to create such compartmentalization are impeded by the compensatory actions of the thermoregulatory system.

In addition, there are situations in which it would be desirable to be able to manipulate the transfer of heat across the skin surfaces to raise or lower the core temperature of the mammalian body en gross to the extremes or beyond a normothermic range. Again, such methodology may be useful for therapeutic treatment regimens, as described in greater detail below. Yet, driving such temperature variations can be difficult. Simply attempting to extract heat from or drive heat into a system without circumventing compensatory actions of the thermoregulatory system produces only limited results (or requires a great deal of effort in overwhelming the system).

As such, there is great interest in the development of methods in which the thermoregulatory system is manipulated so that energy can be transferred into or out of the thoracic/abdominal core body without triggering concomitant opposing reaction by the thermoregulatory system and/or utilizing the thermoregulatory system to aid in the desired out come.

3. Relevant Literature

U.S. Pat. No. 5,683,438. See also WO 98/40039. Also of interest are: Soreide et al., "A non-invasive means to effectively restore normothermia in cold stressed individuals: a preliminary report," J Emerg. Med. (1999 July–August) 17(4):725–30 and Grahn et al., "Recovery from mild hypothermia can be accelerated by mechanically distending blood vessels in the hand," J. Appl Physiol. (1998) 85(5): 1643–8.

SUMMARY OF THE INVENTION

Methods and devices for manipulating the thermoregulatory status of a mammal are provided. In certain of the subject methods, thermal energy is transferred between the environment and both of the thoracic/abdominal and head regions or compartments of the core body of the mammal. In general, thermal energy transfer between the thoracic/abdominal region of the core body and the environment occurs under negative pressure conditions. The subject methods and devices can be used to increase the thoracic/abdominal temperature of a mammal, in which case thermal energy is introduced into this region or compartment of the core body of the mammal and removed from the head of the mammal. The subject methods and devices can also be used to reduce the thoracic/abdominal temperature of a mammal, in which case thermal energy is removed from this region of the core body of the mammal and introduced into the head of the mammal. In these variations of the invention, subject devices include at least the following components: (a) a means for causing a transfer of thermal energy with the thoracic/abdominal region of the core body of a mammal under negative pressure conditions; and (b) a means for causing a transfer of thermal energy with the head region of the core body of the mammal. Such methods and devices find use in a variety of applications, and are particularly suited for use in producing a thermal gradient in a mammal, e.g., one in which the thoracic/abdominal core body is warmer or colder than the head.

Other methods included in the present invention may also involve thermal energy transferred between the environment and the thoracic/abdominal, however, hot or cold applied in at least the region of the head is not be provided for the purpose of transferring energy to or therefrom. Instead, a thermal load applied to the general skin surface, including at least the head region may be employed merely for its affect on the thermoregulatory system. As an aspect of the invention, it has been appreciated that heat applied to at least the head region promotes a drop in core body temperature; conversely, cold applied to at least the head region promotes a raise in core body temperature.

The action is akin to raising or lowering the setting of a thermostat. By a "feed forward" mechanism, the thermoregulatory system changes a set point for core body temperature. Cold applied to the skin in at least the region of the head/face/neck causes an upward adjustment of the set point in response to the stimulus with the set point adjusted upward, heat production is increased and/or the mechanism controlling heat loss are effectively clamped-down. The reverse occurs when relative warmth is applied to sensitive skin regions. The set point is lowered. This result in decreased heat production and/or promotion of heat loss via the skin, even perspiration to actively affect cooling. Such phenomena may be capitalized upon alone in certain treatment methodology disclosed. It may also be maintained and/or leveraged in connection with means for causing a transfer of thermal energy with the thoracic/abdominal region of the core body of a mammal. Maintenance of an induced elevated or lowered temperature hyperthermic or hypothermic state or further driving such a condition in the desired direction is preferably accomplished using a device able to transfer energy to or from the thoracic/abdominal region of the core body under a negative pressure condition.

BRIEF DESCRIPTION OF THE FIGURES

FIGS. 1 to 7 provide various views of a device that can be employed to practice to the subject methods.

DESCRIPTION OF THE SPECIFIC EMBODIMENTS

Figure 1:
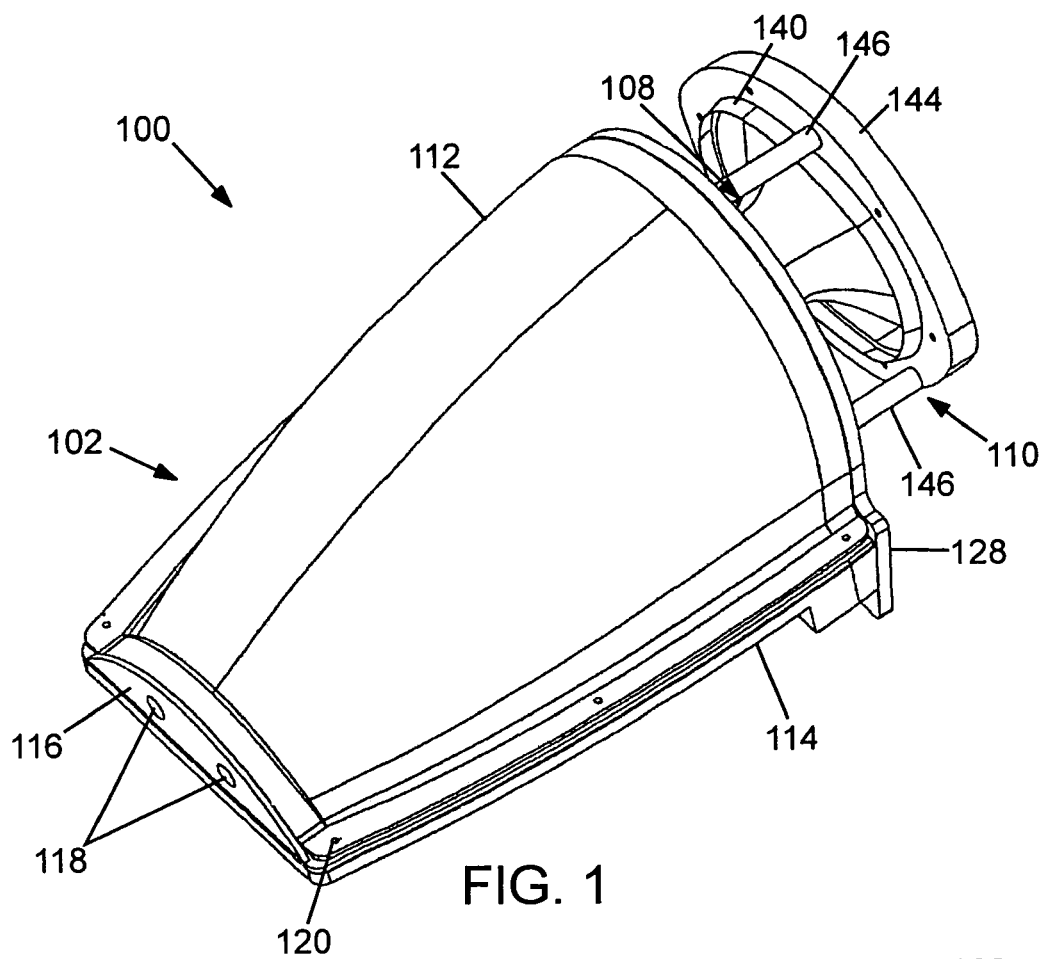

Methods and devices for manipulating the thermoregulatory status of a mammal are provided. In some of the subject methods, thermal energy is transferred between the environment and both of the thoracic/abdominal and head regions of the core body of the mammal. In these methods, thermal energy transfer between the thoracic/abdominal region of the core body and the environment typically occurs under negative pressure conditions. The subject methods and devices can be used to increase the thoracic/abdominal temperature of a mammal, in which case thermal energy is introduced into the thoracic/abdominal region of the core body of the mammal and removed from the head of the mammal. The subject methods and devices can also be used to reduce the temperature of the thoracic/abdominal region of a mammal, in which case thermal energy is removed from the thoracic/abdominal region of the mammal and introduced into the head of the mammal. For practicing these methods, the subject devices or systems include at least the following components: (a) a means for causing a transfer of thermal energy with the thoracic/abdominal region of a mammal under negative pressure conditions; and (b) a means for causing a transfer of thermal energy with the head of the mammal. The subject methods and devices find use in a variety of applications, and are particularly suited for use in altering, changing or modulating the thermalregulatory status of a mammal such that the temperature of the thoracic/abdominal region of the core body of the mammal may be changed relative to the temperature of the head region of the core body of the mammal, typically in ways that are achievable in the absence of practice of the subject invention.

Alternately, similar devices may be used for introducing or extracting thermal energy from the thoracic/abdominal region of the mammal while applying hot or cold to the head region of the mammal (and possibly other regions as well)—not to add or extract heat therefrom, but only to manipulate the thermoregulatory system. The manipulation effected can assist in pumping or drawing even more energy into or our of the core body with the thoracic/abdominal region device. Alternately, heat transfer by the thoracic/abdominal region device may aid in maintaining the condition produced by the manipulation of the thermoregulatory system by the application of hot or cold to al least the region of the head.

In further describing the subject invention, the subject methods and devices will be discussed in greater detail, followed by a review of representative applications in which the subject methods and devices find use. However, before the subject invention is described in such detail, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject methods are directed to methods of manipulating the thermoregulatory state or status of a mammal in one way or another, typically through interaction with the thermoregulatory system of the mammal. By thermoregulatory state or status is meant the distribution of temperatures in the various body parts and regions of the mammal. In some variations of the invention, a compartmentalized distribution of temperatures is produced. In other variations of the invention, core body temperature distributions are adjusted upward or downward substantially together.

By thermoregulatory system is meant the autonomic regulatory system and components thereof that are responsible for temperature maintenance or control in the mammal, particularly maintenance and control of the core body temperature. As such, the thermoregulatory system that is involved in the subject methods is the one responsible for the control of the core body temperature of the mammal under various environmental conditions, e.g., for preventing an increase in core body temperature under warm to hot environmental conditions by increasing heat transfer out of the core body of the mammal and into the environment. The involved thermoregulatory system is also the system that prevents a decrease in core body temperature under cold environmental conditions by decreasing heat transfer out of the core body of the mammal and into the environment. Further, thermoregulatory system action is described above with respect to system "set points" and in connection with certain inventive methodology below.

By manipulate is meant change or modulate, where the nature of the change or modulation is generally to alter the thermoregulatory control and therefore state or status of the mammal in a manner that is not normal or observed in a control situation. In other words, by manipulate is meant to cause the thermoregulatory state or status of the mammal to deviate from normal, for example as represented by room-temperature conditions.

The thermoregulatory system is considered to-be deviant from normal temperatures (or a normothermic state) if temperatures of particular sites in the body core exceed or fall below normal ranges and/or temperature gradients between different sites of the body core exceed normal ranges. Normal temperature ranges for deep core body temperatures are generally from about 35 to 39 and usually 36 to 38° C., where the temperature of the core body is often 37° C. A normal gradient between any two sites in the body core, e.g., between the brain and the heart, brain and abdomen, etc., is generally not greater than about 2° C. in magnitude, usually not greater than about 1° C. in magnitude and often not greater than 0° C. in magnitude.

Despite the breadth of the "normal" range of temperatures spanning as much as 35 to 39° C., for a given set of conditions, core temperatures outside about 1.0 degree of 37° C. may be regarded as hyperthermic, hypothermic or tending toward hyperthermia or hypothermia. For instance, in attempting to re-warming post-anesthetic patients it has been observed that as long as a human body is exposed to very warm air (between about 33 and 35° C.) in a "re-warming" bag, low core body temperatures on the order of 35° C. will not produce shivering; however, upon termination of such stimulus when the core body temperature remains virtually unchanged, violent shivering associated with hypothermia is observed. As such, what may be perceived as normal to the body in the presence of certain external stimuli may represent an undesirably state under alternate external stimuli. Regardless, for the purposes of certain aspects of the invention, "low" core body temperatures mean those less than about 36° C., more preferably less than about 35.5° C. or most preferably less than about 35° C. Conversely, "high" core body temperatures mean those that are above about 38° C., more preferably above 38.5° C. or most preferably above 39° C.

In practicing one set of the subject methods, thermal energy is non-invasively transferred between: (a) the thoracic/abdominal region of the core body of the mammal and the outside of the mammal; and (b) the head region of the core body of the mammal and the outside of the mammal. In another set of the subject methods, significant thermal energy is non-invasively transferred between the thoracic/abdominal region of the core body of the mammal and the outside of the mammal, and relative hot or cold is applied to the general skin surface of at least the head region of the core body in such a manner the preferably results only in insignificant transfer of thermal energy to this region.

Such transferring or application of thermal energy preferably occur at substantially the same time, including simultaneously. Thus, in certain embodiments where the transfers do not occur simultaneously but at substantially the same time, thermal energy transfer/application may alternate between the above disparate regions of the core body, where when it alternates the period of time between any given thermal energy event is preferably of short duration, where by short duration is mean a duration of less than about 15 min, usually less than about 5 min and more usually less than about 1 min. In yet other embodiments, the above described thermal energy transfer or application events occur at substantially the same time, including simultaneously, such that thermal energy is being transferred between the thoracic/abdominal core body and the external environment of the mammal at substantially the same time, if not at the same time, that thermal energy is being applied to or transferred between the head and the external environment of the mammal.

By core body is meant the internal body region or portion of the mammal, as opposed to the surface of the mammal. Specific core body regions of interest are the core body region of the head, e.g., the deep brain region, and the core body region of the trunk of the mammal, e.g., the thoracic/abdominal region of the mammal.

In the subject methods, an energy transfer event with the head is generally opposite of that which occurs with the thoracic/abdominal region. As such, in certain embodiments thermal energy is introduced into the thoracic/abdominal region and it is removed from the head. In other embodiments, thermal energy is removed from the thoracic/abdominal region and introduced into the head. These different embodiments are described in greater detail infra. When thermal energy is transferred between the head and the external environment, it is often transferred to or from venous blood in the head which secondarily exchanges heat with the arterial blood and thereby the core body region of the head. By arterial blood is meant blood present in the main arteries that convey blood from the heart to the head of the mammal.

In alternate methods according to the present invention, thermal energy is introduced into the thoracic/abdominal region and cold is applied at least to the region of the head so to promote a raise in core body temperature. In another variation of the invention, thermal energy is removed from the thoracic/abdominal region and hot/heat is applied to the head so to promote a drop in core body temperature. In either case, the thermal energy applied to the head or head region is preferably not sufficient to introduce or draw energy from the head region so as to produce an appreciable compartmentalization effect (i.e., its effect is insignificant). Again, these different embodiments of the invention are described in greater detail infra.

The above described thermal energy transfer events may be performed with or without the aid of automated data collection and/or processing means. As such, in certain embodiments one or more sensors are employed to detect temperatures in the core body and head region of the mammal. Any convenient temperature sensing means may be employed, where suitable means include: thermocouples, thermosistors, microwave temperature sensors, and the like. The position and nature of the temperature sensing means necessarily depends on whether it is to detect the core body or head temperature of the mammal. For detecting thoracic/abdominal core body temperature, sensor locations of interest include: the esophagus, the rectum, and in the case of microwave detection, anywhere on the surface of the body to measure the underlying temperature. For head temperature, sensor locations of interest include: the auditory canal, the oral cavity, and in the case of microwave detection, anywhere on the surface of the head to measure the underlying temperature. The data collected from these sensor devices may be processed by a processing means to at least display the data for the operator in a user friendly/readable format. The data may also be processed by a processing means which causes or inhibits the thermal energy transfer events in response to the detected data or variations therein.

The subject methods are suitable for use with a variety of mammals. Mammals of interest include, but are not limited to: race animals, e.g., horses, dogs, etc., work animals, e.g., horses, oxen etc., and humans. In most embodiments, the mammals on which the subject methods are practiced are humans.

Specific embodiments of the subject methods include: (a) methods of increasing the thoracic/abdominal core body temperature of a subject; (b) methods of decreasing the thoracic/abdominal core body temperature of a subject; (c) methods of increasing both the thoracic/abdominal core body and head core temperature (i.e., the overall core body temperature) of a subject; and (d) methods of decreasing the overall core body temperature of a subject. Each of these embodiments (and variations thereof) will now be discussed separately in greater detail. However, the below described specific embodiments are merely representative of the different embodiments of the subject invention and are in no way limiting on the scope of the subject invention.

Methods of Increasing Thoracic/Abdominal Core Body Temperature of a Mammal

In this embodiment of the subject invention, the methods are methods of increasing the thoracic/abdominal core body temperature of a mammal. By increasing is meant raising the thoracic/abdominal core body temperature of the mammal by at least some amount, where the amount of increase is generally at least about 0.5, usually at least about 2.0 and more usually at least about 4.0° C. As such, the subject methods can be used to increase the core body temperature of the mammal to a temperature ranging from about 37 to 44, usually from about 38 to 40° C.

In practicing the subject methods of increasing the thoracic/abdominal core body temperature of a mammal, thermal energy is input into the core body of the mammal at substantially the same time, if not the same time, that thermal energy is removed from the head, e.g., the venous blood, of the mammal. In inputting or introducing thermal energy or heat into the thoracic/abdominal core body of the mammal, a surface of the mammal is contacted with a warm temperature medium under negative pressure conditions for a period of time sufficient to achieve the desired amount of heat introduction. The surface that is contacted with the warm temperature medium is generally a heat exchange surface which acts as a heat exchange means between the thoracic/abdominal core body and the environment of the mammal. Heat exchange surfaces of interest with the subject methods include those found in the various regions, and particularly the extremities, of the mammal, e.g., the arms, legs, palms, soles, and the like.

By negative pressure conditions is meant a pressure lower than ambient pressure under the particular conditions in which the method is performed, e.g., 1 ATM at sea level. The magnitude of the decrease in pressure from the ambient pressure under the negative pressure conditions is generally at least about 20 mmHg, usually at least about 30 mmHg and more usually at least about 35 mmHg, where the magnitude of the decrease may be as great as 85 mmHg or greater, but typically does not exceed about 60 mmHg and usually does not exceed about 50 mmHg. When the method is performed at or about sea level, the pressure under the negative pressure conditions generally ranges from about 740 to 675 mmHg, usually from about 730 to 700 mmHg and more usually from about 725 to 710 mmHg.

As mentioned above, the surface of the mammal is contacted with a warm temperature medium under the negative pressure conditions. By warm temperature medium is meant a medium that has a temperature which is sufficient to provide the requisite or desired thoracic/abdominal core body thermal energy input or introduction, i.e., one that is sufficient to provide for the desired amount of thoracic/abdominal core body temperature increase. The nature of the medium may vary, the medium being a temperature controlled solid material, e.g., warming blanket; a liquid; or gas; depending on the particular device employed to practice the subject methods. The temperature of the warm temperature medium may vary as well. The warm temperature medium generally has a temperature ranging from about 42 to 52, usually from about 44 to 50 and more usually from about 46 to 48° C. Whatever the precise temperature, it should be sufficient to break any vaso-constrictive blockade, otherwise interfering with heat introduction.

Contact is maintained for a period of time sufficient for the desired amount of thermal energy input or introduction into the thoracic/abdominal core body to occur. As such, contact is generally maintained for at least about 1 min, usually at least about 2 min and more usually at least about 3 min, where contact may be maintained for up to 10 hrs or longer, but is generally not maintained for longer than 1 day and usually is not maintained for longer than 1 hr.

In practicing the subject methods, the negative pressure conditions during contact may be static/constant or variable. Thus, in certain embodiments, the negative pressure is maintained at a constant value during contact of the surface with the low temperature medium. In yet other embodiments, the negative pressure value is varied during contact, e.g., oscillated. Where the negative pressure is varied or oscillated, the magnitude of the pressure change during a given period may be varied and may range from about −85 to 40 mmHg, usually from about −40 to 0 mmHg, with the periodicity of the oscillation ranging from about 0.25 sec to 10 min, usually from about 1 sec to 10 sec.

In practicing the subject methods, the negative pressure conditions may be provided using any convenient protocol. In many embodiments, the negative pressure conditions are provided by enclosing a portion of the mammal that includes the target surface that is to be contacted with the low temperature medium in a sealed enclosure, where the pressure is then reduced in the sealed enclosure thereby providing the requisite negative pressure conditions. The portion that is enclosed in the sealed enclosure is a portion of the mammal that includes the target heat exchange surface, and therefore is an appendage in many embodiments of the subject invention. As such, the portion that is sealed is an arm or leg, or at least a portion thereof, e.g., hand or foot, in many embodiments of the subject invention. The nature of the enclosure will vary depending on the nature of the appendage to be enclosed, where representative enclosures include gloves, shoes/boots, or sleeves, where the latter is described in greater detail supra in connection with the description of the representative devices that can be used to practice the subject invention.

The magnitude of thoracic/abdominal core body thermal energy introduction accomplished during practice of the methods may vary, and is sufficient to increase the thoracic/abdominal core body temperature of the mammal, as described above. In many embodiments, the magnitude of heat introduction is generally at least about 0.5 Kcal/min, usually at least about 1.0 Kcal/min and more usually at least about 10 Kcal/min, where the magnitude may be as great as 1.5 Kcal/min or greater, but generally does not exceed about 50 Kcal/min and usually does not exceed about 30 Kcal/min. The magnitude of head introduction may, and often will vary depending on whether one is at the beginning of the subject methods or in the middle of the subject methods, e.g., at the start of the method the magnitude is generally greater than during the method, where only maintenance of conditions is required. The period of time that the heat is introduced into the thoracic/abdominal core body may vary, but typically ranges from about 1 min to 24 hrs, usually from about 2 min to 1 hr and more usually from about 2 min to 50 min.

In these embodiments of the subject invention, thermal energy is also removed from the head. In many embodiments, thermal energy is removed from the head arterial blood supply, e.g., carotid arterial blood. Thermal energy may be removed from the arterial blood supply using any convenient protocol, where non-invasive protocols are preferred. In those embodiments where non-invasive protocols are employed to remove thermal energy, one or more surfaces of the mammal, typically associated with or on the head, is contacted with a cooling medium. Locations of interest that may be contacted with the cooling medium include at least: the general skin surface, especially, of at least the head, neck, chest face, ears, and the like. Representative cooling mediums include: cooling solids, e.g., blankets, cooling fluids, cooling gases, etc. The temperature of the cooling medium is a temperature sufficient to provide for thermal energy extraction yet, often, not so great as to cause substantial vasoconstriction in the area of contact. The temperature typically ranges from about 0 to 35, usually from about 10 to 30 and more usually from about 15 to 25° C. The duration of contact is sufficiently long to provide for the desired amount of thermal energy extraction from the head core body region, and typically ranges from about 1 min to 10 hr, usually from 2 min to 5 hr and more usually from about 5 min to 5 hr. In these embodiments, the temperature of the head may or may not decrease. Throughout this specification, the term "head" refers not only to the head itself, but also the neck.

The subject methods of this embodiment may be used to raise the core body temperature of the mammal substantially while causing substantially no temperature change in the head. The magnitude of the temperature increase that can be achieved in the core body using the subject methods typically ranges from about 1 to 10, usually from about 2 to 7° C. to provide for an increased temperature that ranges from 38 to 45, usually from about 39 to 43° C. As there is substantially no change in the temperature of the head, the magnitude of any temperature change in the head, if present, does not exceed about 2, usually does not exceed about 1.5 and more usually does not exceed about 1° C.

Methods of Reducing Thoracic/Abdominal Core Body Temperature of a Mammal

In this embodiment of the subject invention, the subject invention provides methods for reducing the temperature of the thoracic/abdominal body core of a mammal. As mentioned above, by thoracic/abdominal core body is meant the internal body region or portion of the trunk of the mammal, as opposed to the surface of the mammal or the core body portion of the head of the mammal. In extracting thermal energy or heat from the thoracic/abdominal core body of the mammal, a surface of the mammal is contacted with a low temperature medium under negative pressure conditions for a period of time sufficient to achieve the desired amount of heat extraction, while heat is introduced in the head of the mammal. The surface that is contacted with the low temperature medium is generally a heat exchange surface which acts as a heat exchange means between the thoracic/abdominal core body and the environment of the mammal. Heat exchange surfaces of interest with the subject methods include those found in the various regions of the mammal, and particularly appendage (extremities) regions thereof, e.g., the arms, legs, palms, soles, and the like.

As described above, by negative pressure conditions is meant a pressure lower than ambient pressure under the particular conditions in which the method is performed, e.g. 1 ATM at sea level. The magnitude of the decrease in pressure from the ambient pressure under the negative pressure conditions is generally at least about 20 mmHg, usually at least about 30 mmHg and more usually at least about 35 mmHg, where the magnitude of the decrease may be as great as 85 mmHg or greater, but typically does not exceed about 60 mmHg and usually does not exceed about 50 mmHg. When the method is performed at or about sea level, the pressure under the negative pressure conditions generally ranges from about 740 to 675 mmHg, usually from about 730 to 700 mmHg and more usually from about 725 to 710 mmHg.

As mentioned above, the surface of the mammal is contacted with a low temperature medium under the negative pressure conditions. By low temperature medium is meant a medium that has a temperature which is sufficient to provide the requisite or desired core body thermal energy extraction or removal. The nature of the medium may vary, the medium being a temperature controlled solid material, e.g., cooling blanket, a liquid, or gas, depending on the particular device employed to practice the subject methods. The temperature of the low temperature medium may vary, but generally is not so low as to cause local vasoconstriction at the surface of the mammal, e.g., the heat exchange surface. The low temperature medium generally has a temperature ranging from about 0 to 35, usually from about 10 to 30 and more usually from about 15 to 25° C.

Contact is maintained for a period of time sufficient for the desired amount of thoracic/abdominal core body thermal energy extraction or removal to occur. As such, contact is generally maintained for at least about 1 min, usually at least about 2 min and more usually at least about 3 min, where contact may be maintained for up to 10 hrs or longer, but is generally not maintained for longer than 1 day and usually is not maintained for longer than 1 hr.

In practicing the subject methods, the negative pressure conditions during contact may be static/constant or variable. Thus, in certain embodiments, the negative pressure is maintained at a constant value during contact of the surface with the low temperature medium. In yet other embodiments, the negative pressure value is varied during contact, e.g., oscillated. Where the negative pressure is varied or oscillated, the magnitude of the pressure change during a given period may be varied may range from about −85 to 40 mmHg, usually from about −40 to 0 mmHg, with the periodicity of the oscillation ranging from about 0.25 sec to 10 min, usually from about 1 sec to 10 sec.

In practicing the subject methods, the negative pressure conditions may be provided using any convenient protocol. In many embodiments, the negative pressure conditions are provided by enclosing a portion of the mammal that includes the target surface that is to be contacted with the low temperature medium in a sealed enclosure, where the pressure is then reduced in the sealed enclosure thereby providing the requisite negative pressure conditions. The portion that is enclosed in the sealed enclosure is a portion of the mammal that includes the target heat exchange surface, and therefore is an appendage in many embodiments of the subject invention. As such, the portion that is sealed is an arm or leg, or at least a portion thereof, e.g., hand or foot, in many embodiments of the subject invention. The nature of the enclosure will vary depending on the nature of the appendage to be enclosed, where representative enclosures include gloves, shoes/boots, or sleeves, where the latter is described in greater detail supra-in connection with the description of the representative devices that can be used to practice the subject invention.

The magnitude of thoracic/abdominal core body thermal energy extraction accomplished during practice of the methods may vary, and is sufficient to provide for the desired outcome, e.g., reduction in core body temperature. In many embodiments, the magnitude of heat extraction is generally at least about 0.5 Kcal/min, usually at least about 1.0 Kcal/min and more-usually at least about 1.5 Kcal, where the magnitude may be as great as 50 Kcal/min or greater, but generally does not exceed about 30 Kcal/min and usually does not exceed about 20 Kcal/min. As above, the actual magnitude of energy extraction will vary within the above range depending on whether one is at the start of the process or in the middle of the process. The period of time that the heat is extracted from the core body may vary, but typically ranges from about 1 min to 24 hrs, usually from about 2 min to 1 hr and more usually from about 2 min to 50 min.

In these embodiments of the subject invention, thermal energy is also introduced into the head, e.g., via the carotid arterial blood supply or general skin surface. Thermal energy may be introduced into the head using any convenient protocol, where non-invasive protocols are preferred. In those embodiments where non-invasive protocols are employed to introduce thermal energy, the surface of the mammal, typically at a location that can be provide heat exchange with the arterial blood supply and therefore the core body region of the head, is contacted with a warm temperature medium. Locations of interest include: the neck, face, ears and the like. Representative warm temperature mediums include: warm solids, warm liquids and warm gases, etc. The temperature of the warm temperature medium is a temperature sufficient to provide for the desired amount of thermal energy transfer. The temperature typically ranges from about 35 to 52, usually from about 37 to 50 and more usually from about 40 to 48° C. The duration of contact is sufficiently long to provide for the desired amount of thermal energy transfer, and typically ranges from about 1 min to 24 hr, usually from about 2 min to 10 hr and more usually from about 5 min to 2 hr.

The magnitude of thoracic/abdominal core body temperature reduction accomplished during practice of the methods may vary, and is sufficient to provide for the desired outcome. In many embodiments, the magnitude of reduction is generally at least about 0.5° C., usually at least about 1.0° C. and more usually at least about 1.5°, where the magnitude may be as great as 4° C. or greater, but generally does not exceed about 4.0° C. and usually does not exceed about 2.0° C. The period of time that the core body temperature is reduced may vary, but typically ranges from about 1 min to 24 hrs, usually from about 2 min to 10 hrs and more usually from about 5 min to 2 hrs. Even though the thoracic/abdominal core body temperature is decreased, the temperature of the head changes little, if any. Where the temperature of the head does change, the magnitude of the change is less than about 2° C., usually less than about 1° C.

Methods of Increasing Overall Core Body Temperature

In this embodiment of the subject invention, methods are provided for raising the temperature of the thoracic/abdominal and head core of a mammal. The magnitude of such an overall core temperature increase accomplished during practice of this methodology may vary, as is sufficient to provide for the desired outcome. By increasing is meant raising the core body temperature of the mammal in these regions by at least some amount, where the amount of increase is generally at least about 0.5° C., usually at least about 1.0° C. and more usually at least about 1.5°, where the magnitude may be as great as 4° C. or greater, but generally does not exceed about 4° C. and usually does not exceed about 2.0° C. As such, the subject methods can be used to increase the core body temperature of the mammal to a temperature ranging from about 37 to 44, usually from about 38 to 40° C. The period of time that the core body temperature is increased may vary, but typically ranges from about 1 min to 24 hrs, usually from about 2 min to 10 hrs and more usually from about 5 min to 2 hrs.

In introducing thermal energy or heat into the core body of the mammal, a surface of the mammal is preferably contacted with a warm temperature medium under negative pressure conditions for a period of time sufficient to achieve the desired amount of heat introduction, while cold is applied to the head of the mammal (or other regions as well). As in the method for rising the thoracic/abdominal core body temperature described above, the surface that is contacted with the hot or warm temperature medium is generally a heat exchange surface which acts as a heat exchange means between the thoracic/abdominal core body and the environment of the mammal. The same heat exchange surfaces of interest apply, as do preferred negative pressure conditions.

Also, with respect to the thermal energy extraction medium, as above, by high temperature medium it is meant a medium that has a temperature which is sufficient to provide the requisite or desired core body thermal energy addition or introduction. The other aforementioned characteristics of the warm temperature medium apply as well. In addition, contact parameters of the warm thermal medium, including the amount of time, the nature of the negative pressure condition and the protocol by which it is applied may be as described above. Furthermore, the magnitude rate or amount of thoracic/abdominal core body thermal energy extraction accomplished during practice of the methods may vary, but may represent values like those above in terms of overall K cal/min as facilitate by breaking the vasoconstrictive blocade.

In these embodiments of the subject invention, thermal energy (or a medium lacking therein) is also applied to the general surface area including that of at least the head. Preferably, no appreciable or significant transfer of thermal energy thereto occurs. Thermal energy may be applied the head using any convenient protocol. Preferably, the entire head, the face or at least portions of the face are exposed to cool or cold air. Representative cooling mediums include: cooling solids, e.g., blankets, cooling fluids, cooling gases, etc. Skin cooling may be provided simply by way of ambient environmental conditions or by such means as forced air, or contacts with solid or liquid mediums. Selective cooling of the head may be accomplished by wearing or applying insulative material (e.g., clothing) over areas other than the head region. This may help to reduce loss of heat introduced by the abdominal/thoracic device.

Generally, the temperature of the cool or low temperature medium is a temperature sufficient to provide for the desired thermoregulatory system reaction (i.e., raising the system's set point). The temperature may vary greatly. Generally lower temperatures in the range of 5 to 25° C. will produce the desired result. Of particular importance, however, in causing a thermoregulatory reaction that can be used, is that the temperature applied should represent a relatively rapid and significant downward change from the previous temperature exposure. An immediate change is preferred. A change over as many as a few minutes may sometimes also be effective. A change of as little as 5° C. over a previous applied heat condition may be adequate. However, swings in temperature between about 15 and 20° C. may be preferred.

The duration of contact or application of the cold thermal medium to the head depends on the intended treatment regime. While less than a minute of exposure may be sufficient to start the process, contact (or at least periodic contact) should persist as long as core heating is desired. Otherwise, the change (lack or absence) of input stimulus may cause the thermoregulatory system to drive matters in the opposite of the intended direction (e.g., lowering the system's set point).

The intended transmission of heat into the core body per the subject methods, including inducing hypethermia or near-hypethermia, involve the body naturally elevating core body temperatures in response to the cold stimulus applied at least to the region of the head. The thermal energy introduced by the warm thermal medium through the heat exchange surface areas may either push the core body temperature above the temperature that would otherwise occur in reaction to the hot/warm medium, be used to maintain the naturally elevated core temperature condition, or produce a combination of such effects.

While such application of warm/hot and cool mediums can raise the core body temperature in both the thoracic/abdominal and head regions of the mammal, some variance in temperature may be observed between the two. As with the method described above, however, if there is a difference in the core temperature of the head and that of the body the magnitude of any temperature difference, if present, should not exceed about 1° C. and, typically, does not exceed about 0.5° C. When energy transfer to the head region does not produce a greater temperature difference, such energy transfer is considered herein to be an insignificant amount or insubstantial amount.

Methods of Reducing Overall Core Body Temperature

In this embodiment of the subject invention, methods are provided for reducing the temperature of the thoracic/abdominal and head core of a mammal. The magnitude of such an overall core temperature reduction accomplished during practice of this methodology may vary, as is sufficient to provide for the desired outcome. In many embodiments, the magnitude of reduction is generally at least about 0.5° C., usually at least about 1.0° C. and more usually at least about 1.5°, where the magnitude may be as great as 4° C. or greater, but generally does not exceed about 4° C. and usually does not exceed about 2.0° C. The period of time that the core body temperature is reduced may vary, but typically ranges from about 1 min to 24 hrs, usually from about 2 min to 10 hrs and more usually from about 5 min to 2 hrs.

In extracting thermal energy or heat from the core body of the mammal, a surface of the mammal is preferably contacted with a low temperature medium under negative pressure conditions for a period of time sufficient to achieve the desired amount of heat extraction, while heat is applied to the general skin surface, including the head of the mammal (or other regions as well). As in the method for lowering the thoracic/abdominal core body temperature described above, the surface that is contacted with the low temperature medium is generally a heat exchange surface which acts as a heat-exchange means between the thoracic/abdominal core body and the environment of the mammal. The same heat exchange surfaces of interest apply, as do preferred negative pressure conditions.

Again, with respect to the thermal energy extraction medium, by low temperature medium it is meant a medium that has a temperature which is sufficient to provide the requisite or desired core body thermal energy extraction or removal. The other aforementioned characteristics of the low temperature medium apply as well. In addition, contact parameters of the cold thermal medium, including the amount of time, the nature of the negative pressure condition and the protocol by which it is applied may be as described above. Furthermore, the magnitude rate or amount of thoracic/abdominal core body thermal energy extraction accomplished during practice of the methods may vary, but may represent values like those above in terms of overall K cal/min.

In these embodiments of the subject invention, thermal energy is also applied to the general skin surface including at least the head. Preferably, no appreciable or significant transfer of thermal energy thereto occurs. Thermal energy may be applied to the head using any convenient protocol. Preferably, the entire head, the face or at least portions of the face are exposed to warm air. Other warm temperature mediums include: warm solids, warm liquids and other warm gases, etc. The temperature of the warm temperature medium is a temperature sufficient to provide for the desired thermoregulatory system reaction. Skin warming may be provided simply by way of ambient environmental conditions or by such means as forced air, or contacts with solid or liquid mediums. As above, selective application of stimulus to the region of the head is possible, for example, through the use of insulative materials.

The temperature of the warm/hot medium applied may vary greatly. Generally higher temperatures in the range of 25 to 50° C. will produce the desired result. Of particular importance, however, in causing a thermoregulatory reaction that can be used, is that the temperature applied represents a relatively rapid and significant upward change from the previous temperature exposure. An immediate change is preferred. A change over as many as a few minutes may sometimes also be effective. A change of as little as 5° C. over a previous applied heat condition may be adequate. However, swings in temperature between about 15 and 20° C. may be preferred.

The duration of contact or application of warm thermal medium to the head depends on the intended treatment regime. While less than a minute of exposure may be sufficient to start the process, contact (or at least periodic contact) should persist as long as core heating is desired. Otherwise, the change (loss or absence) of input stimulus may cause the thermoregulatory system to drive matters in the opposite of the intended direction.

The intended cooling of the core body in these methods, including inducing hypothermia or near-hypothermia, involve the body naturally dropping or depressing core body temperatures in response to the warm or hot stimulus applied to at least the region of the head. The thermal energy introduced by the cold thermal medium may either push the core body temperature below the temperature that would otherwise occur in reaction to the warm medium, be used to maintain the naturally depressed core temperature condition, or produce a combination of such actions.

While such application of warm/hot and cold mediums can lower the core body temperature in both the thoracic/abdominal and head regions of the mammal, some variance in temperature may be observed between the two. As with the method described above, however, if there is a difference in the core temperature of the head and that of the body the magnitude of any temperature difference, if present, should not exceed about 1° C. and typically does not exceed about 0.5° C. When energy transfer to the head region does not produce a greater temperature difference, such energy transfer is considered herein to be an insignificant amount or insubstantial amount.

Devices/Systems

The above described methods may be practiced using any convenient device. In general, any device that is capable of providing for the desired thermal energy transfer with the head and thoracic/abdominal core body, as described above, may be employed. As such, certain systems according to the present invention include at least a thermal energy transfer element for transferring thermal energy between the thoracic/abdominal core body of a mammal and the environment and a thermal energy transfer element for transferring energy between the head of a mammal and the environment.

The thermal energy transfer element for causing thermal energy transfer with the thoracic/abdominal core body typically includes a warming or cooling element, as described above, and a negative pressure element for providing the negative pressure environment at the thoracic/abdominal core body target heat exchange surface. In many embodiments, this negative pressure element for providing a negative pressure environment includes a sealing element for sealing an appendage of the mammal in an enclosed environment in which negative pressure conditions can be produced. Representative enclosing elements include sleeves, boots/shoes, gloves, etc. which are in operational relationship -with a negative pressure inducing element, e.g., a vacuum, that is capable of producing a negative pressure environment, as described above, in the sealed enclosure. The negative pressure inducing element may be actuated in a number of different ways, including through motor driven aspiration, through a system of valves and pumps which are moved through movement of the mammal in a manner sufficient to create negative pressure in the sealed environment, etc.

As mentioned above, the subject devices also include an element for contacting the heat exchange surface with the warm/cool temperature medium. Representative contacting elements for contacting the surface with a warming or cooling medium include: warming or cooling blankets, warm or cool water immersion elements, warming or cooling gas elements, etc. In many embodiments, the device further includes an element for producing the warm or cool temperature medium, where this element may vary depending on the nature of the warm or cool temperature medium. For example, where the warm temperature medium is a warming blanket whose temperature is modulated by actuation of resistance heating elements in the blanket, this element for producing a warm temperature medium is an electrical current producing element for providing electrical current to the warming blanket. Alternatively, the device may include a fluid operationally connected to a fluid warming element that produces warm fluid which serves as the warming medium. In yet another embodiment, where a cool temperature medium is employed, the device may include a fluid operationally connected to a fluid refrigerant element which produces cool fluid. Alternately, chemical heater and cooling units may be employed.

In addition, the subject devices include a thermal energy transfer element for transferring energy between the head of the mammal and the environment. In many embodiments, this element is specifically designed for transfer of energy between the head arterial blood supply of the mammal and the environment. Any convenient element that accomplishes this purpose may be employed, where the element will be either a cooling element or heating element, as described above. The element may be in any convenient format, e.g., as a collar, hood or other device specifically designed to accomplish thermal energy transfer with at least a portion or region of the head.

In certain embodiments, the devices are adaptations of those devices described in U.S. Pat. No. 5,683,438 and co-pending U.S. patent application Ser. No. 09/839,590; the disclosures of which are herein incorporated by reference. These devices, however, only provide examples of such hardware as may be used in connection with the present invention. Other options are available as well.

FIGS. 1 to 6 provide various view of another embodiment of a device that can be employed to practice the subject invention. The features of the system depicted in FIGS. 1 to 6, belonging to AVACore Technologies, Inc. (Palo Alto, Calif.), are preferred for carrying out the methodologies described herein. The system described includes a negative pressure chamber in which to apply or remove thermal energy from a human subject. An improved interface between the chamber and its external environment is provided.

Aquarius, Inc. (Scottsdale, Ariz.) produces a system that may be used or variously modified for use in the stated method(s). However, that system utilizes a "hard" seal interface with a user. The system described herein may utilize a "soft" seal. A "hard" seal is characterized as one designed to altogether avoid air leakage past the boundary it provides. In theory, a "hard" seal will allow a single evacuation of the negative pressure chamber for use in the methods. In practice, however, a "hard" seal can produce a tourniquet effect. Also, any inability to maintain a complete seal will be problematic in a system requiring as much.

A "soft" seal as described herein is characterized as providing an approximate or imperfect seal at a user/seal interface. Such a seal may be more compliant in its interface with a user. Indeed, in response to user movement, such a seal may leak or pass some air at the user/seal interface. In a negative-pressure system designed for use with a soft seal, a regulator or another feedback mechanism/routine will cause a vacuum pump, generator, fan or any such other mechanism capable of drawing a vacuum to respond and evacuate such air as necessary to stabilize the pressure within the chamber, returning it to the desired level. Active control of vacuum pressure in real-time or at predetermined intervals in conjunction with a "soft" seal provides a significant advantage over a "hard" seal system that relies on simply pulling a vacuum with the hopes of maintaining the same.

A further disadvantage over the Aquarius system has more to do with seal configuration than its barrier function. Entry and exit from the Aquarius seal is difficult. Whether "hard" or "soft" in function, the present system provides a two-sided seal configuration. The meaning of this will be more apparent in view of the following figures and descriptive text.

Figure 2:
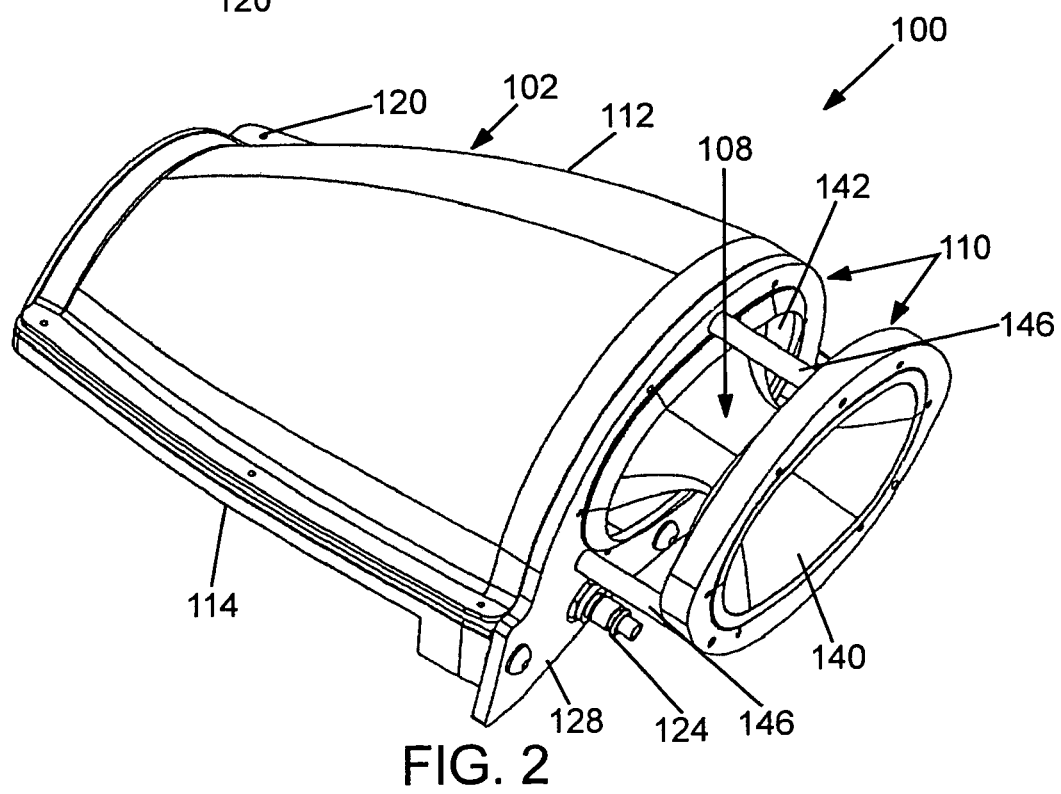
Figure 3:
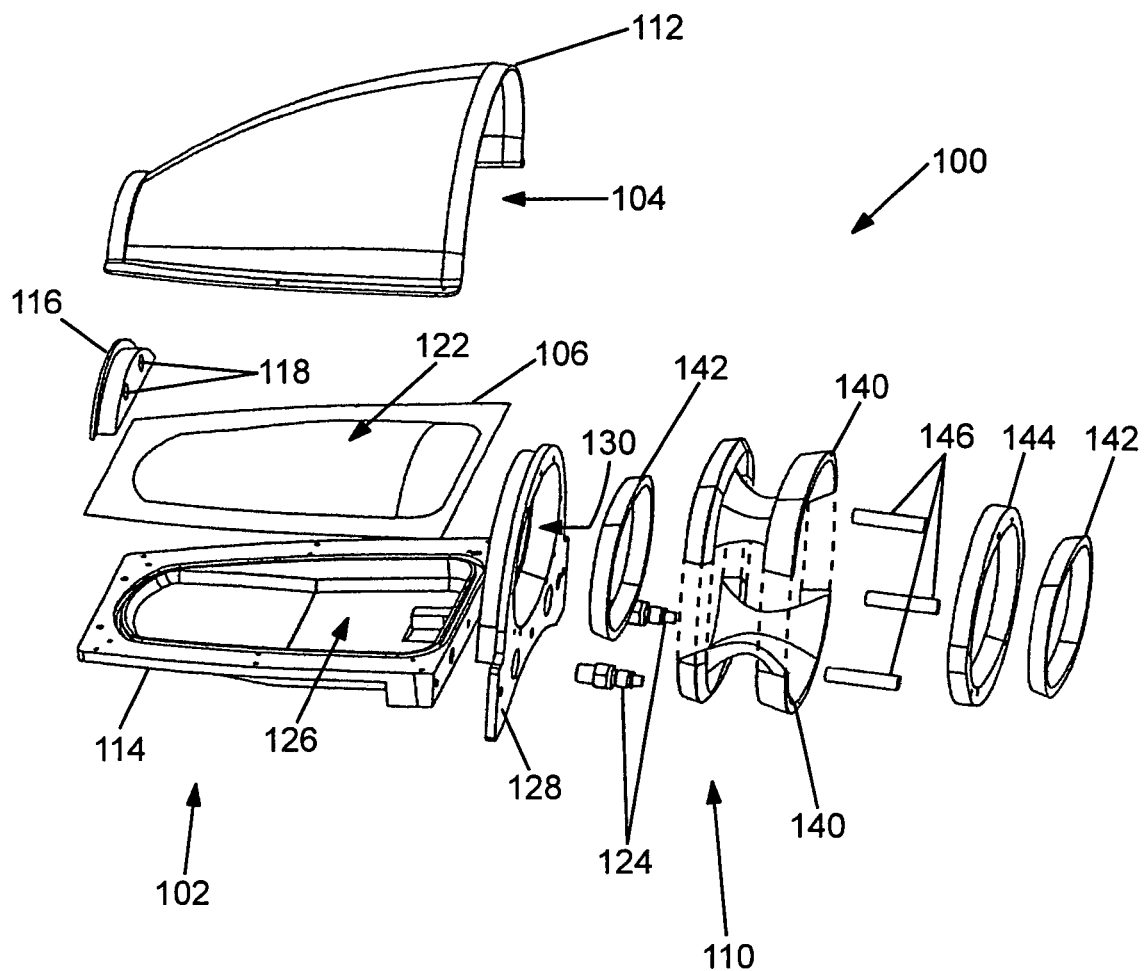

FIGS. 1 and 2 provide fore and aft perspective views of a negative pressure thermal exchange module (100). FIG. 3 provides an exploded view of the same. The system components not shown in the figures include a thermal control or perfusion unit. Such a unit may be adapted to provide a stream of heat exchange media such as water at elevated temperatures, lowered temperatures or both. Further, a vacuum source and regulator optionally used with module (100) are not shown. Any sort of vacuum source or regulator/control mechanism may be used with module (100) as would be apparent to one with skill in the art. Together, these components work to maintain a pressure within module (100) during use between about 20 and 25 inches of H2O (37 to 47 mmHg) and temperatures for core body cooling between about 19 and 22° C., sometimes lower, or temperatures for core body heating between about 40 and 45° C., sometimes higher.

As shown, module (100) includes a housing (102) defining a negative pressure chamber (104), a heat-exchange element (106) and a soft, two-sided seal (108) supported by seal frame elements (110).

Housing (102) may be made from a cover (112) and a base (114). Negative pressure chamber (104) is preferably provided between heat exchange element (106) and cover (112). The embodiment shown is adapted to fit the hand of a human user. Chamber (104) is preferably configured to fit a human hand of any size. In order to provide a more space-efficient package, however, it may be more preferably sized to fit 95% of human hand sizes. Alternately, it may be sized for more particularized groups, such as children. It is also contemplated that the housing may be configured to fit a human foot since the under surface of a foot may also be used effectively as a heat exchange surface.

Housing (102) may be constructed from multiple pieces, including an end cap (116) as shown, or it may be provided as a unitary structure. Cap (116) is shown including a ports (118). A first port may be utilized for connection to a vacuum source, while the second may be utilized for a vacuum gauge. Of course, alternate port placement is also possible.

Preferably, housing (102) is made of plastic. Most preferably, the material and design of at least a portion of module (100) are such that housing (102) may be produced by vacuum forming or molding techniques.

Where discrete cover (112) and base (114) portions are used, they may be mechanically secured to one another through bolt holes (120). In such an instance, a gasket or caulking may be employed to seal the periphery of housing (102).

Providing a separable cover (112) and base (114) or heat exchange element (106) provide advantageous access to clean module (100) after use. However, it is contemplated that the top and bottom portions of the module may be fused together, for instance, by ultrasonic welding, chemical bonding-or otherwise. Also, as noted above, it is contemplated that housing (102) may be provided in a single piece.

Regardless of the construction, sizing or overall appearance of housing (102), it defines a portion of chamber (104). A heat exchange surface (122) for delivering or accepting a thermal load from a user also defines a portion of chamber (104). A user may directly contact heat exchange surface (122). Alternately, a user may wear a glove or sock or take other prophylactic measures. Heat exchange surface (122) may be provided by a member separate from heat exchange member (106) such as by an intermediate layer of foil, metalized Mylar or another material.

Heat exchange element (106) is preferably made of aluminum or another high thermally-conductive material. It may be in communication with a Peltier device, a desiccant cooling device or an endothermic or exothermic chemical reaction to provide a temperature variance. More preferably, however, heat exchange member (106) is in communication with at an inlet and an outlet (124) to accommodate a flow of perfusion liquid behind heat exchange surface (122). Chilled or heated water may be used to maintain the contact surface of the element at a desired temperature. Perfusion fluid may be run through a series of switchbacks in cavity (126) between element (106) and base (114).

A rear portion of housing (102) and heat exchange member (106) may be provided by plate (128). As depicted, this portion may include provision for inlet and outlet (124) to heat exchange cavity (126) and an opening (130) to chamber (104). A preferred manner of constructing seal (108) is disclosed in connection with plate (128).

Figure 4:
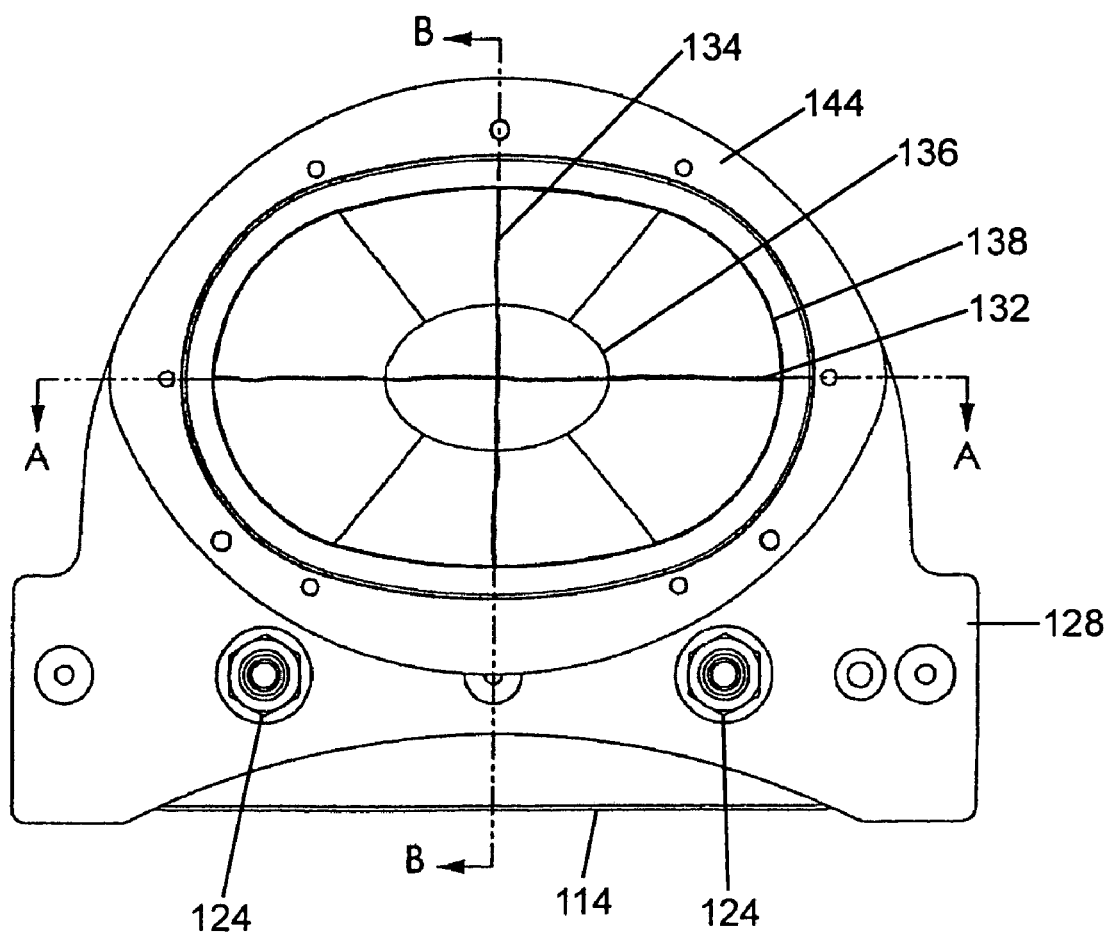

Views detailing preferred geometric aspects of seal (108) are shown in FIGS. 4, 5 and 6. FIG. 4 shows an end-on view of seal (108). Preferably, at least portions of seal (108) are ovalized in form. An elliptical shape may be preferred. A circular shape may also be used. Still, a shape having a major axis (132) and a minor axis (134) will be preferred, at least for the waist opening (136) of seal (108). An ovalized shape approximately corresponds to the shape of the wrist or forearm of a user. A shape having a major axis (132) and a minor axis (134) will also be preferred at chamber opening (130) and seal opening (138). This will assist in providing clearance for hand entry and exit of module (100). It will also simplify the construction of seal webbing (140).

Whether or not ovalized features are utilized for seal (108), it will be shaped roughly like an hourglass. Seal (108) will most closely resemble an hourglass if openings (130), (136) and (138) are circular. When ovalization is applied, different projected views of seal (108)—such as viewed in FIG. 5, for the section taken along line A—A and in FIG. 6 for the section taken along line B—B—display an hourglass shape.

Of course, the shapes depicted may be characterized as other than "hourglass" forms. For instance, profiles of seal (108) may be viewed as hyperbolic or parabolic. Further, simple radiused or semi-circular cross-sections may be utilized in producing seal (108). Further straightened sections may be used, especially, between the openings (130) and (138) and waist (136).

Whatever the case, a two-sided seal with outside openings of a greater size than that of the inside opening is to be used in module (100). This geometry provides for ramps or transition sections for appendage entry and exit. These features assist in stretching the seal interface or waist (136) sufficiently wide to pass a hand or foot both for insertion into and removal from module (100).

Material selection is important in providing such a seal. The material must be able to stretch. Further, it should provide a substantial barrier to air flow. To meet each of these criteria, a urethane-backed lycra available from Malden Mills (Malden, Mass.) has proven effective. Still, it is contemplated that other materials may be used. The material (or materials) selected for webbing (140) preferably has a finish that does not grip onto a user so as to complicate entry and exit from module (100). The urethane skin of the referenced material has a satin finish. This decreases friction with the skin and hair of a user.

In addition to providing sufficient stretch, the seal webbing material should also have sufficient strength to avoid being drawn too far into cavity (104) upon the application of vacuum. When in use, the open construction of seal (108) will result in cavity-side webbing material exposed to partial vacuum within chamber (104) to be forced by ambient pressure inward. This self-inflation phenomena observed for the chamber-side of the seal may be of assistance in providing seal patency with a user. However, if too much material bows inward, it will result in an uncomfortable or disconcerting displacement of the user's hand or foot into the device. Accordingly, with proper material choice, the side of seal (108) opposite chamber (104) provides not only a transition section for entry and exit, but also a stabilizing feature for seal position.

Seal (108) is preferably formed by a sleeve made by stitching two pieces of webbing material (140) together where they are shown broken apart in the exploded view of FIG. 3. By constructing the sleeve from two or more pieces, complex shapes can be easily produced. To secure the sleeve webbing (140) in place to form seal (108), it is folded over rings (142) at each end as variously depicted. Then the cavity-side ring and webbing is captured in opening (130) of plate (128). The opposite side of seal webbing (140) is captured between outer ring (142) and retainer member (144). Standoffs (146) or equivalent structure space plate (128) and ring retainer (144) apart to define the overall length of seal (108). Of course, the length of the standoffs or seal may be varied as well as the other parameters of seal (108) that effect fit.

In this respect, it is noted that it may be desirable to provide a longer overall seal in some instances. Increasing overall length provides further design flexibility with seal shape. This may be best taken advantage of by increasing the length of waist (134) to provide greater seal surface contact with a user. This may beneficially reduce any undesirable constricting effects. Furthermore, it is to be appreciated that the nature of the material used for the seal webbing (140) may be advantageously varied. While the noted lycra-based material is isotropic in nature, an anisotropic material or effect may be preferred for the webbing. This is to say that greater radial expansion of the sleeve may be desirable, whereas longitudinal compliance may not be. By reducing compliance along the axis of the sleeve relative to a radial component, it will tend to be drawn into chamber (104) to a lesser degree upon the application of vacuum. For a very high-stretch material, this will allow for smaller seal openings to fit the same population (since they can still stretch webbing (140) radially and have it return sufficiently to form a desired seal), without forfeiting the full set of advantages that the two-sided seal described offers.

Such an anisotropic effect may be achieved in a number of ways. It may be accomplished by providing longitudinal reinforcement member(s) associated with the webbing. They may be incorporated through braiding techniques, by bonding/affixing stiffener(s) to the sleeve surface or by other means as would be apparent to one with skill in the art.

Regardless of the particulars of seal construction and whether it is utilized to provide a "hard" or "soft" user interface, the dual-sided seal disclosed provides a superior manner of carrying out the methodology noted above. Though a "soft" two-sided seal as shown in the figures is preferred for its elegance in approach and proven effectiveness, a "hard" or more complex "soft" seal approach might sometimes be desired.

In order to utilize the dual-sided seal in a "hard" approach, supplemental forcing means may be provided-to apply pressure around seal waist (134). Mechanical means such as at least one of a strap, belt or cinch may be used. Alternately an inflatable cuff or bladder portions around the periphery of the seal may be employed. While the system complexity will increase due to provision for providing the supplemental pressure and controlling it by either automated or manual means, certain potential advantages arise. It may enable a single-evacuation procedure for chamber (104) rather than relying on constant or periodic vacuum replenishment. It may also provide greater design flexibility for seal (108). Particularly, by providing another variable to utilize in design decisions, a lesser emphasis may be placed on webbing material choice or opening sizing since the supplemental forcing capacity may be used to shape the seal as desired in use. Further, it may enable fitting seal (108) to a wider range of a populous for a given configuration of hard elements, such as those that make-up seal frame (110).

Supplemental forcing or seal shaping means may also be used to produce a more complex "soft" seal than that described above. As with a "hard" seal approach, this would open design and fit possibilities. Forcing or seal shaping parameters may, again, be controlled manually or automatically. Except, in a complex "soft" seal, the control of pressure applied to waist (134) is gauged to provide a compliant feel or fit. Since the application of pressure on the seal interface with the user may be the only difference between a complex "soft" seal approach and a "hard" seal approach utilizing the dual-sided configuration, the same apparatus may be configured to function in either manner, for instance, by providing variable pressure control.

Figure 7:
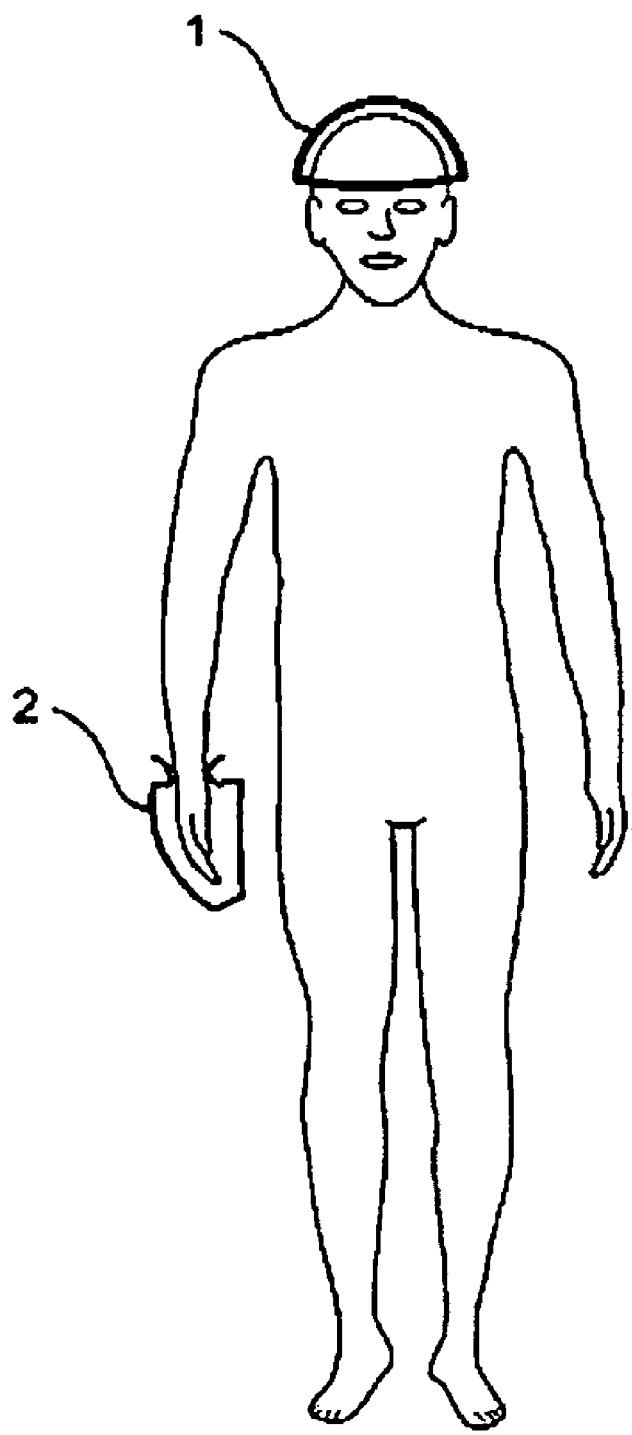

FIG. 7 provides a view of another embodiment of a device that can be employed in practicing embodiments of the invention. In the embodiment shown in FIG. 7, a device for causing a transfer of thermal energy with the head of a mammal (1) and a device for causing a transfer of thermal energy with the thoracic/abdominal core body of a mammal (2) is shown.

In certain embodiments, one or more of the various components of the device are typically actuatable, i.e., turned on and off, by a control means which controls actuation of the various components in response to the detected head and/or thoracic/abdominal core body temperature of the mammal and, in certain embodiments, changes in the temperatures of the bodily compartments. The control means is generally a processing means that is capable of taking output data from the head and thoracic/abdominal core body temperature sensing means, processing the data to determine whether or not the negative pressure means/warming or cooling means should be actuated or not and then actuating these components of the device accordingly.

UTILITY

The subject methods find use in any application in which the manipulation of the thermoregulatory status of a mammal is desired. The subject methods are particularly well suited for causing the temperature of various core body compartments, e.g., the thoracic/abdominal core body region, and/or the one or more temperature gradients in the mammal to deviate from normal, as described above. Two representative embodiments in which the subject methods find use are in methods of increasing the thoracic/abdominal core body temperature of a subject and in methods of decreasing the thoracic/abdominal core body temperature of a subject. There are many situations where the induction of selective hyperthermia is desirable, including the treatment of disease conditions, e.g., cellular proliferative diseases, including cancer and the like, where the subject methods may be used in conjunction with one or more additional treatment therapies, e.g., chemotherapy, radiation, etc. By selective hyperthermia is meant thoracic/abdominal core body hypothermia, e.g., a situation where the thoracic/abdominal core body temperature is significantly higher than the head temperature, e.g., at least by a magnitude of about 2, usually about 5° C. The subject methods of increasing the core body temperature of a mammal find use in the treatment of cellular proliferative diseases, e.g. cancer In addition, there are other situations where the selective cooling of the core body temperature is desired. As such, the subject methods are suitable for use in a variety of different applications, where core body heat extraction is desirable. Representative applications in which the subject methods of reducing the thoracic/abdominal core body temperature find use include the treatment of chronic disease conditions, e.g., of cystic fibrosis symptoms, treatment of multiple sclerosis symptoms, and the like. By treatment is meant at least an alleviation in one or more of the symptoms associated with the condition being treated, e.g. a reduction in discomfort, amelioration or elimination of symptoms, etc.

Furthermore, there are situations in which it is desirably to heat the whole of the core body which includes the head and thoracic/abdominal core body. In these methods, treatment of disease conditions such as viral diseases (e.g. HIV and Hepatitis, where heat kills transformed cells to decrease viral load) cellular proliferation diseases, including cancer may be treated as in the methods of heating the thoracic/abdominal core body above. The hyperthermia generated may be of assistance with additional therapies such as chemotherapy, radiation, etc, as above. However since whole-body temperature elevations is possible, treatments of the brain or other head/neck regions are additionally facilitated. It is noted that such treatments may be accomplished with cold stimulus applied to at least the head region, without abdominal/thoracic heat removal. For some applications, such as low-dose radiation, the raise in body/set point change possible employing this aspect of the invention alone may offer significant benefit.

Also, there are situations in which it is desirable to cool the whole of the core body which includes the head and thoracic/abdominal core body. In these methods, treatment of disease conditions such as cystic fibrosis and multiple sclerosis symptoms is possible. As compared to the core body cooling methods above, since the head is also cooled in these methods where no substantial or very little energy is absorbed by the head region, stroke and MI treatment is also possible. As in the methods described directly above the treatment methodology described herein may be accomplished with thoracic/abdominal heat transfer devices or assistance. Changing the thermoregulatory system set point by applying heat/hot to at least the head region may be adequate for treatment. For example, it may offer a simple, rapid response to the onset of stroke or hyperthermia. In a counter intuitive fashion, heat (preferably hot air) may be applied to a heat-exhausted subject to promote a drop in body temperature.

Whereas convention wisdom might dictate removing an overheated subject to a cold environment, it has been appreciated by the inventors hereof that the cold stimulus to the body may produce an inadvertent thermoregulatory reaction counter to the intended cooling. It is believed this reaction can actually result in death, as certain publicized examples illustrate.

In other circumstances, however, where it is desired to raise core body temperature (for example as a rapid response to hypothermia) cold may be applied to the general skin surface including at least the region of the head to promote a beneficial thermoregulatory system response to raise body temperature. Conversely, when it is desired to lower core body temperature (for example as a rapid response to hyperthermia) hot/warm may be applied to the general skin surface including at least the region of the head to promote a beneficial thermoregulatory system response to lower core body temperature.

It is evident from the above results and discussion that the subject invention provides a convenient means for manipulating the thermoregulatory system of a mammal. Specifically, the subject invention provides a non-invasive and convenient way to induce hypo- or hyperthermia in the head core body and/or thoracic/abdominal core body of a mammal. Since the subject methods and devices provide for differential temperature regulation of the head with respect to the core body, more effective changes in core body temperature can be achieved in an easier manner, as the thermoregulatory system of the host is bypassed or leveraged, at least to a partial extent. In view of the above advantages and large number of different types of applications in which the subject invention may be employed, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for increasing the thoracic/abdominal core body temperature of a mammal, said method comprising:
   contacting a surface of a portion of said mammal with a warm temperature medium under negative pressure conditions for a period of time sufficient to introduce thermal energy into the thoracic/abdominal core body of said mammal, and
   removing thermal energy from the head of said mammal;
   wherein the thoracic/abdominal core body temperature of said mammal is increased.

2. A method for decreasing the thoracic/abdominal core body temperature of a mammal, said method comprising:
   contacting a surface of a portion of said mammal with a cold temperature medium under negative pressure conditions for a period of time sufficient to remove thermal energy from the thoracic/abdominal core body of said mammal, and
   introducing thermal energy into the head of said mammal;
   wherein the thoracic/abdominal core body temperature of said mammal is decreased.

3. The method of claim 2, wherein said period of time ranges from about 5 to 600 mm.

4. A method for manipulating the thermoregulatory status of a mammal, said method comprising:
   causing a transfer of thermal energy with the head of said mammal under negative pressure conditions, and
   causing a transfer of thermal energy with the thoracic/abdominal core body of said mammal,
   wherein said thermoregulatory status of said mammal is manipulated.

5. The method of claim 4, wherein a non-compartmentalized thermoregulatory status is produced.

6. A method for manipulating the thermoregulatory status of a mammal, said method comprising:
   causing a transfer of thermal energy with the thoracic/abdominal core body of said mammal, and
   applying thermal energy to the head of said mammal so as to transfer an insignificant amount of thermal energy thereto,
   wherein any transfer of thermal energy to said head is opposite that with said thoracic/abdominal core, and
   wherein said thermoregulatory status of said mammal is manipulated such that said thermal energy application to said head produces a thermoregulatory system response in the direction of said assisting said thermal energy transfer with the thoracic/abdominal core body.

7. A method for manipulating the thermoregulatory status of a mammal, said method comprising:
   causing a transfer of thermal energy with the thoracic/abdominal core body of said mammal under negative pressure conditions, and
   causing a transfer of thermal energy with the head of said mammal, opposite said transfer with said thoracic/abdominal core,
   wherein said thermoregulatory status of said mammal is manipulated.

8. The method of claim 7, wherein said transfers of thermal energies produce a compartmentalized thermoregulatory status.

9. The method of claim 7, wherein said transfer of energy with said head is of an insignificant amount so as to produce an overall change in thermoregulatory status.

10. A method for increasing core body temperature of a mammal, said method comprising:
    contacting a surface of a portion of said mammal with a warm temperature medium under negative pressure conditions for a period of time sufficient to introduce thermal energy into the thoracic/abdominal core body of said mammal, and applying a cold temperature medium to the head of said mammal, wherein at least the thoracic/abdominal core body temperature of said mammal is increased.

11. The method of claim 10, wherein only the thoracic/abdominal core body temperature increases substantially.

12. The method of claim 10, wherein both thoracic/abdominal and head core body temperatures increases substantially.

13. A method for increasing core body temperature of a mammal, said method comprising:

contacting a surface of a portion of said mammal with a cold temperature medium under negative pressure conditions for a period of time sufficient to introduce thermal energy into the thoracic/abdominal core body of said mammal, and applying a warm temperature medium to the head of said mammal, wherein at least the thoracic/abdominal core body temperature of said mammal is decreased.

14. The method of claim 13, wherein only the thoracic/abdominal core body temperature decreases substantially.

15. The method of claim 13, wherein both thoracic/abdominal and head core body temperatures decreases substantially.

16. The method of claim 13, wherein the warm temperature medium is air.

17. A system for manipulating the thermal regulatory status of a mammal, said system comprising:

an enclosure for producing a negative pressure condition when enclosing a portion of a mammal, an energy application medium adapted for transferring energy with said portion, and an energy application medium adapted for applying energy to the head of a mammal.

18. The system of claim 17, wherein said portion of said mammal is a limb or portion thereof.

19. The system of claim 18, wherein said limb is selected from the group consisting of an arm and a leg.

20. The system of claim 17, wherein said energy application medium adapted for transferring energy with said portion is adapted for transferring thermal energy to the thoracic/abdominal core body of said mammal.

21. The system of claim 17, wherein said energy application medium adapted for transferring energy with said portion is adapted for transferring energy from the thoracic/abdominal core body of said mammal.

22. The system of claim 17, wherein said energy application medium for applying energy with said head is adapted for transferring thermal energy to said head.

23. The system of claim 17, wherein energy application medium for applying energy with said head is adapted for transferring thermal energy form said head.

24. The system of claim 17, wherein said energy application medium for applying energy with said head of a mammal is air.

25. The system of claim 24, wherein said air is colder than said energy application medium adapted for transferring energy within said portion.

26. The system of claim 24, wherein said air is warmer than said energy application medium adapted for transferring energy within said portion.

27. The system of 25, further comprising an negative pressure generator, wherein said generator is capable of producing a negative pressure ranging from about −20 to −80 mm Hg.

* * * * *

UNITED STATES PATENT AND TRADEMARK OFFICE
CERTIFICATE OF CORRECTION

PATENT NO. : 7,182,776 B2 Page 1 of 1
APPLICATION NO. : 10/932344
DATED : February 27, 2007
INVENTOR(S) : Dennis A. Grahn et al.

It is certified that error appears in the above-identified patent and that said Letters Patent is hereby corrected as shown below:

In claim 3, col. 22 line 20 please replace the word

"mm" with -- min. --

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

PATENT NO.        : 7,182,776 B2
APPLICATION NO.   : 10/932344
DATED             : February 27, 2007
INVENTOR(S)       : Grahn et al.

Page 1 of 1

It is certified that error appears in the above-identified patent and that said Letters Patent is hereby corrected as shown below:

In the Specification:

- In Column 1, prior to the Introduction beginning on line 16, insert the following header and paragraph:

--FEDERALLY SPONSORED RESEARCH AND DEVELOPMENT

This invention was made with Government support under contract NBCH1030020 awarded by The Department of the Interior, contract M67854-00-C-2144a, awarded by the Marine Corps Systems Command, and contracts DAMD17-03-2-0029, W911NF-05-1-0548, W911NF-07-1-0098 awarded by The Department of the Army. The Government has certain rights in this invention.--

Signed and Sealed this
Eleventh Day of October, 2011

David J. Kappos
*Director of the United States Patent and Trademark Office*